United States Patent
Harrèus et al.

(10) Patent No.: US 7,758,657 B2
(45) Date of Patent: Jul. 20, 2010

(54) COMPOSITION FOR COLOURING KERATIN FIBRES

(75) Inventors: Julia Harrèus, Weinheim (DE); Jonathan Wood, Weinheim (DE); Anja Aechtner, Mannheim (DE); Bernd Nöcker, Tokyo (JP)

(73) Assignee: KPSS-KAO Professional Salon Services GmbH, Darmstadt (DE)

( * ) Notice: Subject to any disclaimer, the term of this patent is extended or adjusted under 35 U.S.C. 154(b) by 0 days.

(21) Appl. No.: 12/102,609

(22) Filed: Apr. 14, 2008

(65) Prior Publication Data

US 2009/0038085 A1 Feb. 12, 2009

(30) Foreign Application Priority Data

Apr. 20, 2007 (EP) .................................. 07008090

(51) Int. Cl.
*A61Q 5/10* (2006.01)
(52) U.S. Cl. ....................... 8/405; 8/406; 8/435; 8/594; 8/607; 8/620
(58) Field of Classification Search .................. 8/405, 8/406, 435, 594, 607, 620
See application file for complete search history.

(56) References Cited

U.S. PATENT DOCUMENTS 7,204,861 B2 * 4/2007 Marsh et al. ................... 8/405

FOREIGN PATENT DOCUMENTS

EP 1 232 741 A1 * 8/2002

OTHER PUBLICATIONS

English Abstract of the Patent No. EP 1 232 741 A1 (2002).*
STIC Search Report dated Apr. 9, 2009.*

* cited by examiner

*Primary Examiner*—Eisa B Elhilo
(74) *Attorney, Agent, or Firm*—Norris, McLaughlin & Marcus

(57) ABSTRACT

Present invention relates to a coloring composition for keratin fibers especially for hair, and, especially for brightening hair. Coloring composition of the present invention for keratin fibers especially human hair based on oxidative dye precursors and optionally comprising coupling agents and direct dyes comprises further at least one carbonate at a concentration of 0.75 to 5% by weight, at least one ubiquinone at a concentration of 0.001 to 1%, at least one aminated silicone at a concentration of to 1% by weight and at least one chelating agent at a concentration of 0.25 to 5 % by weight, all concentrations are calculated to total composition and prior to mixing with a composition comprising oxidizing agent.

10 Claims, No Drawings

COMPOSITION FOR COLOURING KERATIN FIBRES

Present invention relates to a colouring composition for keratin fibres especially for hair, and, especially for brightening hair.

Hair colouring is a common practice for many decades. Especially oxidative colouring hair is one of the preferred way when long lasting colours are wished. Brightening hair with oxidative treatment other than bleaching has been employed in cases wherein wished lighter colour is in the distance of 4 and 5 levels from the colour before lightening and wherein the wished lighter colour is not achievable by bleaching due to missing counteraction.

In oxidative colouring, one of the problems is different colours are obtained depending on the physicochemical state of the hair. In other words, hair colour obtained at the root part of the hair where hair is healthier is different from the colour towards tips where hair is more damaged with environmental influences such as light, gasses and frequent washing. This brings about problems since the target is a even colouration throughout whole length of hair. It has further been observed in the practice, this problem is aggravated in brightening hair colour, i.e. target hair colour is lighter than the original hair colour.

It has surprisingly and unexpectedly found out by the present inventors, an oxidative hair colouring compositions based on oxidative dyes reacting to form coloured molecules in the presence of oxygen colours hair evenly when it comprises at least one carbonate, at least one ubiquinone, at least one aminated siliocne and at least one chelating agent.

EP 1232741 discloses oxidative colouring compositions with coenzyme Q10. EP 1166750 discloses oxidative dyeing compositions with organosiloxane compounds. Both documents do not deal with brightening hair evenly.

Thus, the subject matter of the present invention is oxidative colouring composition for hair based on oxidative dye precursors and optionally comprising coupling agents and direct dyes comprising at least one carbonate at a concentration of 0.75 to 5% by weight, at least one ubiquinone at a concentration of 0.001 to 1%, at least one aminated silicone at a concentration of 0.01 to 1% by weight and at least one chelating agent at a concentration of 0.25 to 5% by weight, all concentrations are calculated to total composition and prior to mixing with a composition comprising oxidizing agent.

Further subject matter of the present invention is use of a colouring composition based on oxidative dye precursors and optionally comprising coupling agents and direct dyes comprising at least one carbonate at a concentration of 0.75 to 3% by weight, at least one ubiquinone at a concentration of 0.001 to 1%, at least one aminated silicone at a concentration of 0.01 to 2% by weight and at least one chelating agent at a concentration of 0.25 to 5% by weight, all concentrations are calculated to total composition and prior to mixing with a composition comprising oxidizing agent for colouring hair, especially brightening hair.

Further subject matter of the present invention is use of a colouring composition based on oxidative dye precursors and optionally comprising coupling agents and direct dyes comprising at least one carbonate at a concentration of 0.75 to 3% by weight, at least one ubiquinone at a concentration of 0.001 to 1%, at least one aminated silicone at a concentration of 0.01 to 2% by weight and at least one chelating agent at a concentration of 0.25 to 5% by weight, all concentrations are calculated to total composition and prior to mixing with a composition comprising oxidizing agent for brightening hair at least 4 tones.

Compositions of the present invention comprise at least one carbonate. Carbonates suitable for the compositions of the present invention are in principal any water soluble carbonates with monovalent cation. Examples are sodium, potassium ammonium carbonates and sodium, potassium and ammonium bicarbonates. Preferred are sodium, ammonium carbonates and sodium, ammonium bicarbonates. The most preferred are sodium and ammonium bicarbonates.

Concentration of carbonates are in the range of 0.75 to 5% by weight, preferably 0.9 to 3% by weight and most preferably 0.9 to 2% by weight, calculated to total composition and prior to mixing with a composition comprising oxidizing agent.

Composition of the present invention comprise at least one ubiquinone of the general formula

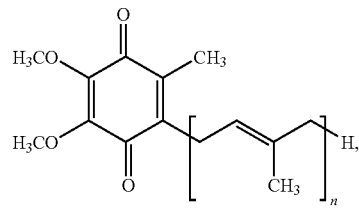

wherein n is 1 to 10. Preferred compound of the formula is ubiquinone 10 wherein n is 10 which is also known as Coenzyme Q10.

Concentration of at least one ubiquinone is in the range of 0.001 to 1% by weight, preferably not more than 0.75% by weight and more preferably not more than 0.5% by weight, calculated to total composition prior to mixing with a composition comprising oxidizing agent.

Compositions of the present invention comprise at least one aminated silicone. The term aminated silicone refers to any silicone compound carrying at least one primary, secondary, tertiary and/or quaternary nitrogen atom in its molecule within the meaning of the present invention. Examples to aminated silicones are amodimethicone, polysilicone-9, quaternium-80 and silicone quaternium-18.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

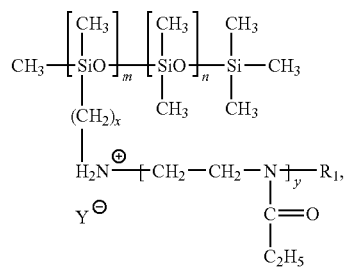

wherein m and n each are numbers from 20 to 10,000, in particular 50 to 7,000, especially 100 to 5,000, x is a number between 1 and 5, preferably 3, and y is a number from 5 to 30, $R_1$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. Most preferred is the one known with the CTFA name Polysilicone-9.

Concentration of at least one aminated silicone in the compositions of the present invention varies between 0.01 and 2% by weight, preferably 0.05 and 1.5% by weight, more preferably 0.05 and 1% by weight, calculated to total composition prior to mixing with a composition comprising oxidizing agent.

Compositions of the present invention comprise at least one chelating agent. In principal any chelating agent is suitable for the purposes of the present invention. Preferred chelating agent is ethylene diamine tetra acetic acid (EDTA) and any salt of it. Most preferred salt is sodium salt.

Chelating agents are included at a concentration of 0.25 to 5% by weight, preferably 0.3 to 3% and more preferably 0.5 to 2% by weight calculated to total composition prior to mixing with a composition comprising oxidizing agent.

Compositions of the present invention comprise oxidative dyes precursors, also known as developing substances. In principal any developing substance is suitable for the purposes of the present invention. Examples to the developing substances are phenylenedimanine and its derivatives such as 2,5-diamino-toluene, 2-n-propyl or 2-ethyl-p-phenylene-diamine, 2,6-dimethyl-p-phenylenediamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene or the water-soluble salts thereof, 4-hydroxy-2-methylaniline, 4-amino-2-methylphenol, tetraaminopyrimidines, in particular 2,4,5,6-tetraaminopyrimidine and the lower alkyl derivatives thereof, triaminohydroxypyrimidines such as 4-hydroxy-2,5,6-triaminopyrimidine, 2-hydroxy-4,5,6-triaminopyrimidine and 5-hydroxy-2,4,6-triaminopyrimidine, mono- and diamino dihydroxypyrimidines such as 2,6-dihydroxy-4,5-diaminopyrimidine, 2,4-diamino-6-hydroxy-pyrimidine or 4,6-dihydroxy-2,5-diaminopyrimidine or the water-soluble salts thereof, aminophenol derivatives such as 4-aminophenol, 4-amino-3-methylphenol, 2-chloro-4-aminophenol, 2,6-dichloro-4-aminophenol, 2,4-diamino-phenol, 2,6-dibromo-4-aminophenol and/or 2-aminophenol and water-soluble salts thereof, and pyrazole derivatives such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 1-methyl-4,5-diaminopyrazole, 1-methylethyl-4,5-diaminopyrazole, 1-phenylmethyl-4,5-diaminopyrazole, 1-methyl-4,5-diaminopyrazole, 1-(4-methylphenyl)methyl-4,5-diaminopyrazole, 1-methyl-3-phenyl-4,5-diaminopyrazole and the water-soluble salts.

The total concentration of the oxidation dyestuff precursors and/or their water soluble salts customarily ranges between about 0.01% and 5%, preferably 0.05% and 4%, in particular 0.1% to 3% by weight, calculated to the total hair dyeing composition (excluding the oxidation agent), whereby these figures are always related to the proportion of free base.

In further preferred form of the present invention especially for brightening hair lower concentrations are especially suitable in the range of 0.01 to 0.5% by weight, preferably 0.05 to 0.25% by weight, calculated to the total hair dyeing composition prior to mixing with a composition comprising oxidizing agent whereby these figures are always related to the proportion of free base.

The composition according to the invention preferably comprises at least one coupling substance, which can be selected from resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3.5-dimethoxypyridine, 2-methyl-5-hydroxyethyl aminophenol, 2-amino-4(β-hydroxyethyl)aminoanisol, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl) amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 2,6-dihydroxyethylamino toluene, 5-amino-2-methoxyphenol and/or 1-methoxy-2-amino-4-(2'-hydroxyethyl amino)benzene or the water-soluble salts thereof.

In the hair dyeing compositions according to the invention, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition (excluding the oxidizing agent), whereby these figures are always related to the proportion of free base.

Here again, in preferred form of the present invention especially for brightening hair, lower concentrations are especially suitable in the range of 0.01 to 0.5% by weight, preferably 0.05 to 0.25% by weight, calculated to the total hair dyeing composition prior to mixing with a composition comprising oxidizing agent whereby these figures are always related to the proportion of free base.

The weight proportion of the developing substances to the coupling substances in general ranges between about 1:8 to 8:1, preferably about 1:5 to 5:1, in particular 1:2 to 2:1 and most preferably 1:1.

Compositions of the present invention comprise preferably one or more direct dye selected from anionic, cationic and neutral ones or their mixtures.

Any cationic direct dye is in principal suitable for the compositions of the present invention. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

According to the invention the suitable anionic direct dyes are: Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Neutral dyes (HC dyes), so called nitro dyes for shading purposes are also optionally contained in the compositions of the present invention. Suitable ones are HC Blue No.2, HC Blue No.4, HC Blue No.5, HC Blue No.6, HC Blue No.7, HC Blue No.8, HC Blue No.9, HC Blue No.10, HC Blue No.11, HC Blue No.12, HC Blue No.13, HC Brown No.1, HC Brown No.2, HC Green No.1, HC Orange No.1, HC Orange No.2, HC Orange No.3, HC Orange No.5, HC Red BN, HC Red No.1, HC Red No.3, HC Red No.7, HC Red No.8, HC Red No.9, HC Red No.10, HC Red No.11, HC Red No.13, HC Red No.54, HC Red No.14, HC Violet BS, HC Violet No.1, HC Violet No.2, HC Yellow No.2, HC Yellow No.4, HC Yellow No.5, HC Yellow No.6, HC Yellow No.7, HC Yellow No.8, HC Yellow No.9, HC Yellow No.10, HC Yellow No.11, HC Yellow No.12, HC Yellow No.13, HC Yellow No.14, HC Yellow No.15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Preferred is that the composition comprises at least one neutral direct dye at the concentration given below.

Concentration of one or more direct dyes in total is in the range of 0.001 to 5% by weight, preferably 0.01 to 3% more preferably 0.05 to 2% by weight calculated to total composition prior to mixing with a composition comprising oxidizing agent.

Here again in composition designed for brightening hair colour lower concentrations are preferred. In such cases concentration of one or more direct dyes is in the range of 0.001 to 0.2% by weight calculated to total composition prior to mixing with a composition comprising oxidizing agent.

Compositions of the present invention can be in the form of solution, dispersion, emulsion, gel and other known forms in the art. The compositions as such and the ingredients for preparing such compositions known in the art. Briefly, compositions of the present invention can comprise surfactants, also emulsifier at the same time, of anionic, cationic, amphoteric and nonionic character, gelling agents of anionic, cationic, amphoteric and nonionic character, fatty acids, alkalizing agents such as ammonia, monoethanolamine, fragrance, solubilizers, organic solvents, conditioning agents.

Hair dyeing is carried out within the scope of the present invention wherein a composition according the present invention based on oxidative dye precursors and optionally comprising coupling agents and direct dyes comprising at least one carbonate at a concentration of 0.75 to 5% by weight, at least one ubiquinone at a concentration of 0.001 to 1%, at least one aminated silicone at a concentration of 0.01 to 1% by weight and at least one chelating agent at a concentration of 0.25 to 5% by weight, all concentrations are calculated to total composition and prior to mixing with a composition comprising oxidizing agent, is mixed with a composition comprising an oxidizing agent, preferably hydrogen peroxide, prior to application and then applied onto hair. Processing time is usually 15 to 45 min at ambient temperature or at a temperature between 30 and 45° C. After the processing time lapsed the hair is rinsed off.

Compositions of the present invention is mixed with a composition comprising at least one oxidizing agent at a weight ratio of 3:1 to 1:3 preferably 2:1 to 1:2 and more preferably 1:1. The preferred oxidizing agent is hydrogen peroxide, at a concentration of 2 to 12% by weight. However, the use of other peroxides such as urea peroxide and melamine peroxide is also possible.

The pH-value of the ready-to-use hair dyeing composition, i.e. after mixing with peroxide, can be between 5 and 12, preferably 6-11, more preferably 6.8 to 10.

Composition of the present invention is provided to consumers in the form of a kit comprising separately packed dyeing composition (A) based on oxidative dye precursors and optionally comprising coupling agents and direct dyes comprising at least one carbonate at a concentration of 0.75 to 5% by weight, at least one ubiquinone at a concentration of 0.001 to 1%, at least one aminated silicone at a concentration of 0.01 to 1% by weight and at least one chelating agent at a concentration of 0.25 to 5% by weight, all concentrations are calculated to total composition and prior to mixing with a composition comprising oxidizing agent, and an oxidizing composition (B) comprising at least one oxidizing agent, preferably hydrogen peroxide.

The following example is to illustrate the invention, but not to limit.

| | | (% by wt.) |
|---|---|---|
| Stearyl alcohol | 12.0 | |
| Stearamide MEA | 4.0 | |
| Cocamide MEA | 2.0 | |
| Propylene glycol stearate SE | 4.0 | |
| Sodium lauryl sulfate | 0.3 | |
| Oleic acid | 2.0 | |
| 1,2-Propanediol | 1.5 | |
| Na-EDTA | 0.5 | |
| Sodium sulfite | 1.0 | |
| Ammonium bicarbonate | 0.95 | |
| Ascorbic acid | 0.2 | |
| Perfume | 0.4 | |
| Ammonia, 25% | 1.0 | |
| Ammonium chloride | 0.5 | |
| Polysilicone-9 | 0.15 | |
| Coenzyme Q10 | 0.001 | |
| 2,5-diaminotoluene sulphate | 0.015 | |
| 3-Aminophenol | 0.001 | |
| 2-Methylresorrcinol | 0.005 | |
| 4-hydroxy2-methylaniline | 0.01 | |
| Resorcinol | 0.005 | |
| Water | ad 100.00 | |

The above composition was mixed with an oxidizing lotion comprising 12% by weight hydrogen peroxide in water at a weight ratio of 1:1 and the mixture was applied onto hair with a colour level of 6. After processing 30 min at 40° C., the hair was washed with water and shampooed once. A shiny, even colour lighter than level 10 was observed. It was especially evident that regrowth (root) was in the same colour as the length (middle and towards tip) of the hair.

Excluding ammonium bicarbonate, sodium EDTA, polysilicone-9 and Coenzyme Q10 led to a uneven colouration, the regrowth area was significantly darker than the length.

In another test, two hair tresses having a base colour of 6 were used. One of the tresses was permanently shaped with a commercially available permanent shaping kit before carrying out the colouration. Both tresses, one is natural, coloured with a composition according to example above. For comparative purposes a composition not comprising ammonium bicarbonate, sodium EDTA, polysilicone-9 and Coenzyme Q10 was prepared. The coloration was carried out as described above. The colour difference was significantly larger between the tresses permanently shaped and natural hair coloured with comparative composition whereas between the tresses coloured with inventive composition no difference was observed.

The above results show that with the inventive composition even colouration is achieved.

The invention claimed is:

1. Colouring composition for keratin fibres especially human hair based on oxidative dye precursors and optionally comprising coupling agents and direct dyes characterised in that it comprises at least one carbonate at a concentration of 0.75 to 5% by weight, at least one ubiquinone at a concentration of 0.001 to 1%, at least one aminated silicone at a concentration of 0.01 to 1% by weight and at least one chelating agent at a concentration of 0.25 to 5% by weight, all concentrations are calculated to total composition and prior to mixing with a composition comprising oxidizing agent.

2. Composition according to claim 1, wherein at least one carbonate is selected from sodium, potassium ammonium carbonates and sodium, potassium and ammonium bicarbonates.

3. Composition according claim 1, wherein at least one ubiquinone is according to formula

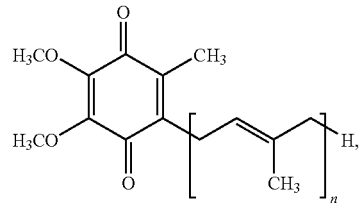

wherein n is between 1 and 10.

4. Composition according to claim 1, wherein at least one aminated silicone is selected from primary any silicone compound carrying at least one primary, secondary, tertiary and/or quaternary nitrogen atom in its molecule.

5. Composition according to claim 4, wherein aminated silicone is selected from amodimethicone, polysilicone-9, quaternium-80 and silicone quaternium-18.

6. Composition according to claim 1, wherein chelating agent is ethylene diamine tetra acetic acid (EDTA) and any salt of it.

7. Composition according to claim 1, wherein it comprises at least one coupling agent.

8. Composition according to any of the preceding claims, wherein it comprises at least one direct dye selected from anionic, cationic and neutral dyes.

9. Process for colouring and/or brightening keratin fibres especially hair characterised in that a composition according to claim 1 is mixed with an oxidizing composition at a weight ratio of 1:3 to 3:1 and applied onto hair and processed for 15 to 45 min at a temperature ranging from ambient temperature to 45° C. and rinsed off from hair.

10. Kit for colouring keratin fibres especially human hair comprising separately packed an oxidative colouring composition according to claim 1 and an oxidizing composition comprising at least one oxidizing agent.

* * * * *